(12) United States Patent
Carlton et al.

(10) Patent No.: US 8,024,045 B2
(45) Date of Patent: Sep. 20, 2011

(54) MULTI-FUNCTIONAL BURR HOLE ASSEMBLY

(75) Inventors: Keith Carlton, Cleveland, OH (US); Alan Greszler, Bay Village, OH (US); Scott Kokones, Cleveland, OH (US)

(73) Assignee: Intelect Medical, Inc., Cleveland, OH (US)

( * ) Notice: Subject to any disclaimer, the term of this patent is extended or adjusted under 35 U.S.C. 154(b) by 660 days.

(21) Appl. No.: 12/028,085

(22) Filed: Feb. 8, 2008

(65) Prior Publication Data

US 2009/0203983 A1 Aug. 13, 2009

(51) Int. Cl.
*A61N 1/36* (2006.01)

(52) U.S. Cl. .......... 607/45; 600/378

(58) Field of Classification Search .......... 604/175; 606/129–130, 114, 378; 607/115–116, 45, 607/139, 149; 600/378, 386
See application file for complete search history.

(56) References Cited

U.S. PATENT DOCUMENTS

| | | | |
|---|---|---|---|
| 6,321,104 B1 | 11/2001 | Gielen et al. | |
| 6,324,433 B1 | 11/2001 | Errico | |
| 6,413,263 B1 | 7/2002 | Lobdill et al. | |
| 6,427,086 B1 * | 7/2002 | Fischell et al. | 607/45 |
| 6,463,328 B1 * | 10/2002 | John | 607/45 |
| 6,574,498 B1 | 6/2003 | Gilboa | |
| 7,050,855 B2 | 5/2006 | Zeijlemaker et al. | |
| 7,174,219 B2 | 2/2007 | Wahlstrand et al. | |
| 7,548,775 B2 * | 6/2009 | Kipke et al. | 600/378 |
| 7,787,945 B2 * | 8/2010 | Greene | 600/544 |
| 2003/0083724 A1 | 5/2003 | Jog et al. | |
| 2003/0088303 A1 | 5/2003 | Goode | |
| 2004/0176673 A1 * | 9/2004 | Wahlstrand et al. | 600/377 |
| 2005/0015128 A1 | 1/2005 | Rezai et al. | |
| 2005/0107753 A1 | 5/2005 | Rezai et al. | |
| 2005/0228249 A1 | 10/2005 | Boling | |
| 2006/0129204 A1 | 6/2006 | Pless et al. | |
| 2006/0247684 A1 | 11/2006 | Halperin et al. | |
| 2007/0208352 A1 | 9/2007 | Henderson et al. | |
| 2007/0265683 A1 * | 11/2007 | Ehrlich | 607/55 |
| 2008/0071313 A1 * | 3/2008 | Stevenson et al. | 607/2 |

FOREIGN PATENT DOCUMENTS

| | | |
|---|---|---|
| WO | 2002/045795 | 6/2002 |
| WO | 2003/028521 | 4/2003 |
| WO | 2004/084749 | 10/2004 |
| WO | 2006/031317 | 3/2006 |

OTHER PUBLICATIONS

PCT US2009/030520 International Search Report and Written Opinion mailed Oct. 15, 2009.

* cited by examiner

*Primary Examiner* — Carl H Layno
*Assistant Examiner* — Paula J Stice
(74) *Attorney, Agent, or Firm* — Kenyon & Kenyon LLP (57) ABSTRACT

A burr hole assembly for use in neurosurgery. In one aspect, the burr hole assembly comprises a burr hole portion and one or more sensors, such as EEG sensors, temperature sensors, intracranial pressure sensors, or motion sensors. In certain embodiments, an input/output unit, which may include a multiplexer, provides a coupling between the sensors and a brain stimulation system which operates in cooperation with the burr hole assembly. In another aspect, the burr hole assembly comprises a burr hole portion and a rotation mechanism which operates in cooperation with an electrode lead. In certain embodiments, the burr hole assembly includes a control system for controlling the rotation mechanism. Also disclosed are systems comprising a burr hole assembly and various components of a brain stimulation system, such as pulse generators, electrode leads, lead extension, or external control systems.

38 Claims, 5 Drawing Sheets

MULTI-FUNCTIONAL BURR HOLE ASSEMBLY

TECHNICAL FIELD

The present invention relates to medical devices, and in particular, burr hole devices for use in neurosurgery.

BACKGROUND

In keeping pace with the continuing advances in deep brain stimulation techniques, neurostimulation systems are becoming increasingly more complex as they incorporate more advanced functionalities. One such functionality is real-time feedback of the patient's response to the deep brain stimulation. For example, a neurostimulation system might use a pulse generator and lead assembly to deliver electrical pulses to the brain, and additionally, an electroencephalogram (EEG) apparatus to monitor the resulting brain activity, which would be provided as feedback to the neurostimulation system. However, the neurostimulation system and the EEG apparatus are separate units that reside on different platforms. With the increasing number of advanced functionalities that are being added to neurostimulation systems, there is a need for an alternate platform to support these multiple modalities.

SUMMARY

In one aspect, the present invention provides a burr hole assembly that operates in cooperation with a brain stimulation system, wherein the burr hole assembly comprises: a burr hole portion; and one or more sensors associated with the burr hole portion, wherein the sensors are for monitoring a patient's clinical status and are capable of being coupled to the brain stimulation system.

In another aspect, the present invention provides a burr hole assembly for operating in cooperation with an electrode lead having one or more directional electrodes, wherein the burr hole assembly comprises: a burr hole portion; and a rotation mechanism to rotate the electrode lead.

In yet another aspect, the present invention provides a system comprising: an electrode lead; a burr hole portion for receiving the electrode lead; a pulse generator for providing stimulation pulses to the electrode lead; one or more sensors coupled to the pulse generator; and an input/output unit for providing a coupling between the sensors and the pulse generator, and a coupling between the pulse generator and the electrode lead.

In yet another aspect, the present invention provides a system comprising: an electrode lead having one or more directional electrodes; a burr hole portion for receiving the electrode lead; and a rotation mechanism associated with the burr hole portion and connected to the electrode lead.

DETAILED DESCRIPTION

In many neurosurgical procedures, such as deep brain stimulation, the brain is accessed through burr holes that are cut in the patient's skull. After the procedure is completed, the burr hole is covered with a burr hole cap to protect the burr hole, and in the case of deep brain stimulation, to secure an electrode lead that is inserted into the brain. As such, embodiments of the present invention provide various burr hole assemblies that serve as a platform for various functionalities that are useful in deep brain stimulation.

Burr hole assemblies of the present invention include a burr hole portion designed to fit within or over a burr hole that is made in the patient's skull. The burr hole portion can include one or more of various components that are conventionally used to cover burr holes, including burr hole caps, burr hole rings, burr hole bases, burr hole shafts, or combinations thereof. For example, a burr hole portion may have a burr hole shaft that is inserted into the burr hole, a burr hole ring that is fits around the shaft, and a burr hole cap that covers the burr hole ring. These various parts may form a single unitary structure or be separate units that are combined to form the burr hole portion.

In a first aspect of the present invention, the burr hole assembly comprises one or more sensors for monitoring a patient's clinical status. Any of various sensors could be used in the burr hole assembly, including intracranial pressure sensors, temperature sensors, motion sensors, cardiovascular sensors, EEG sensors, force sensors (e.g., strain gauges or pressure gauges), etc. The sensor may be associated with the burr hole portion in any of various ways. For example, the sensor may be mounted on, attached to, linked or connected to, or incorporated into the burr hole portion. Also, the burr hole portion and the sensor may form a single unitary structure or the two components may be separate units that are combined to form the burr hole assembly.

The sensor may be located on any of various parts of the body, including internal or external parts of the body. The sensor is capable of being coupled with other components in a deep brain stimulation system (e.g., a pulse generator, patient programmer, or clinician programmer). As used herein, the terms "coupled" or "coupling" refers to a signaling relationship between the components in question, including direct connection or contact (e.g., via an electrically or optically conductive path), radio frequency (RF), infrared (IR), capacitive coupling, and inductive coupling to name a few. The coupling can carry a signal in any direction, including input or output, and can be used for any of various purposes, including transmitting operating power, receiving signals, or transmitting signals. Operating power for the sensors could be provided in any of various ways, including battery power or an external energy source, which may be provided through a physical connection (e.g., wires) or by electromagnetic energy (e.g., RF energy).

In some cases, the sensor is an electroencephalogram (EEG) sensor for detecting the patient's brain wave activity. Multiple EEG sensors may be used to provide greater sensing resolution in different parts of the brain. Information obtained from the EEG sensors (e.g., brain activity, sleep cycles, etc.) could be used to assess the brain's response to the deep brain stimulation.

In some cases, the sensor is a motion sensor which can be placed on the patient's head, extremities, or other body parts. This feature may be useful in providing information about the rehabilitation of the patient's motor function. For example, the patient's leg motion can be detected to determine the patient's response to various stimuli in the regions of the brain that control lower extremity motor function. Multiple motion sensors may be used to determine rotational or relative movement. Various types of motion sensors can be used in the burr hole assembly, including motion sensors that detect acceleration (e.g., acceleration sensors).

In some cases, the sensor is a temperature sensor used to measure body and/or ambient temperature associated with particular tasks the patient is performing. In some cases, the sensor is an intracranial pressure sensor to monitor intracranial pressures inside the patient's skull. In some cases, the sensor is a force sensor (e.g., a pressure sensor to be pushed by the patient or a strain gauge to be pulled by the patient) for measuring the strength of a patient. These and other sensors could also be used in combination to obtain a comprehensive assessment of the patient's response to the treatment.

The burr hole assembly is designed to operate in cooperation with a brain stimulation system, which can include various components, including a pulse generator, an electrode lead, a lead extension, and/or an external control system (e.g., a patient programmer or clinician programmer). Any of various pulse generators, electrode leads, lead extensions, and/or external control systems in a conventional brain stimulation system can be used together with the burr hole assembly. For example, the burr hole assembly can operate with pulse generators that are implantable, programmable with various stimulation modes, or able to communicate with beside monitors, external monitors, or external control systems, such as the patient programmer described in U.S. patent application Ser. No. 11/873,842 (filed 17 Oct. 2007), entitled "Patient Programmer With Input and Sensing Capabilities," which is incorporated by reference herein in its entirety. The pulse generator may also be powered by any of various power sources (e.g., a battery or an external energy source), have an external communication system, an external recharging system, and/or an on-board microprocessor for controlling the brain stimulation system.

The burr hole assembly can also operate with any of various electrode leads that are conventionally used in deep brain stimulation, including electrode leads having directional electrodes or multiple electrodes. As used herein, a "directional electrode" refers to an electrode on an electrode lead in which the electrode extends less than 360° about the body of the electrode lead. The burr hole assembly can also operate with any of various lead extensions which provide electrical connectivity between the pulse generator and the burr hole assembly, including those described in U.S. patent application Ser. No. 11/832,148 (filed Aug. 1, 2007) entitled "Stimulation Extension With Input Capabilities," which is incorporated by reference herein in its entirety. As used herein, "electrical connectivity" refers to an electrical pathway that provides one or more links in a physical connection (e.g., a wire or electrical contact) between two components.

The sensor is coupled to the pulse generator in any of various ways, including a wireless linkage (e.g., radio-frequency) or a physical connection (e.g., by wire or fiber optic line). For example, a wire that travels in parallel with the lead extension or that is contained in the lead extension could connect the sensor to the pulse generator. In certain embodiments, the burr hole assembly includes an input/output unit for providing a coupling between the various components of the brain stimulation system. The input/output unit includes an electrode lead interface and a pulse generator interface for providing electrical connectivity with the electrode lead and the pulse generator (in some cases, via a lead extension extending from the pulse generator), respectively. As used herein, the term "interface," when referring to the input/output unit, means a physical structure that provides electrical connectivity with the input/output unit. As such, an interface may comprise ports, male/female or plug/socket configurations, wires, electrical contacts, or any other type of adaptor that provides a physical electrical connection. Each interface may have one or more channels. For example, the pulse generator interface may have one channel for receiving stimulation pulses from the pulse generator and another channel for communicating with the pulse generator. In some cases, the input/output unit further includes a sensor interface for providing electrical connectivity with the sensors.

In certain embodiments, the input/output unit includes a multiplexer for selectively providing electrical connectivity between the various interfaces on the input/output unit. As such, the multiplexer may be used to direct signal traffic between the various components of the burr hole assembly and the brain stimulation system. This feature may be useful in reducing the number of wires and/or connections between the various components of the burr hole assembly and the brain stimulation system, and thereby, reduce the size of the burr hole assembly.

Various types of multiplexers are suitable for use in the input/output unit, including analog or digital multiplexers. By directing the signal traffic, the multiplexer plays a role in the cooperation between the various components of the burr hole assembly and the brain stimulation system. For example, the multiplexer may selectively provide an electrical connection between the pulse generator interface and the electrode lead interface (e.g., to create an electrical pathway for transmitting stimulation pulses to the electrodes on the electrode lead). Also, for example, where the input/output unit includes a sensor interface with multiple channels, the multiplexer may selectively provide electrical connectivity between each of channels in the sensor interface and the pulse generator (e.g., to create an electrical pathway for communicating with the pulse generator).

Figure 1:
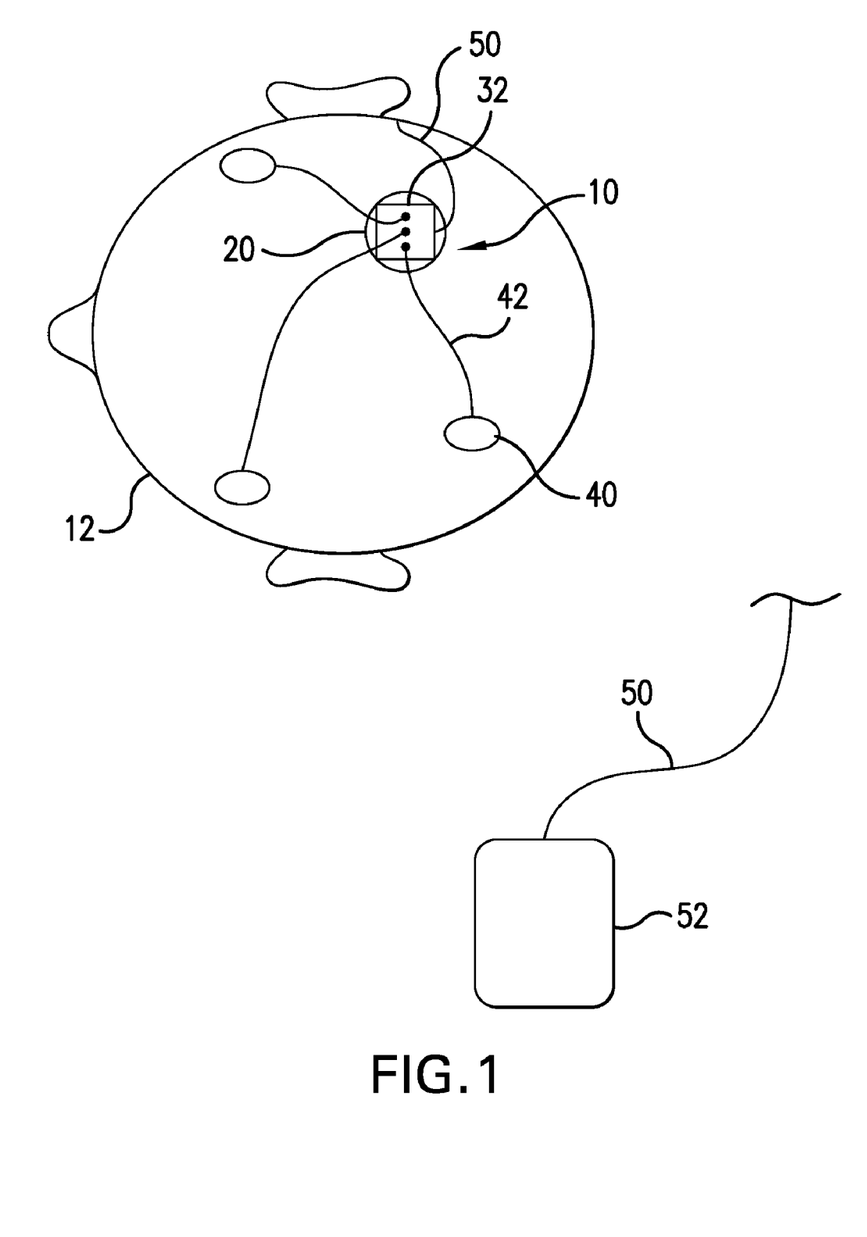
FIG. 1 shows an example of a burr hole assembly according to an embodiment of the present invention, as mounted on a patient's head.

FIGS. 1-4 show a burr hole assembly 10 according to an embodiment of the present invention. FIG. 1 shows burr hole assembly 10 mounted subcutaneously on a patient's head 12. Burr hole assembly 10 includes a burr hole portion comprising a burr hole cap 20 and a burr hole base 22 (see FIGS. 2 and 3), with an input/output unit 32 mounted on the burr hole cap 20. A plurality of EEG sensors 40 are positioned subcutaneously on patient's head 12. EEG sensors 40 are electrically connected to input/output unit 32 via signal wires 42. A lead extension 50, which travels in a subcutaneous tunnel created by blunt dissection, connects an electrode lead 44 (see FIGS. 2 and 3) via input/output unit 32 to a pulse generator 52 implanted in a subcutaneous pocket in the patient's chest area.

Figure 2:
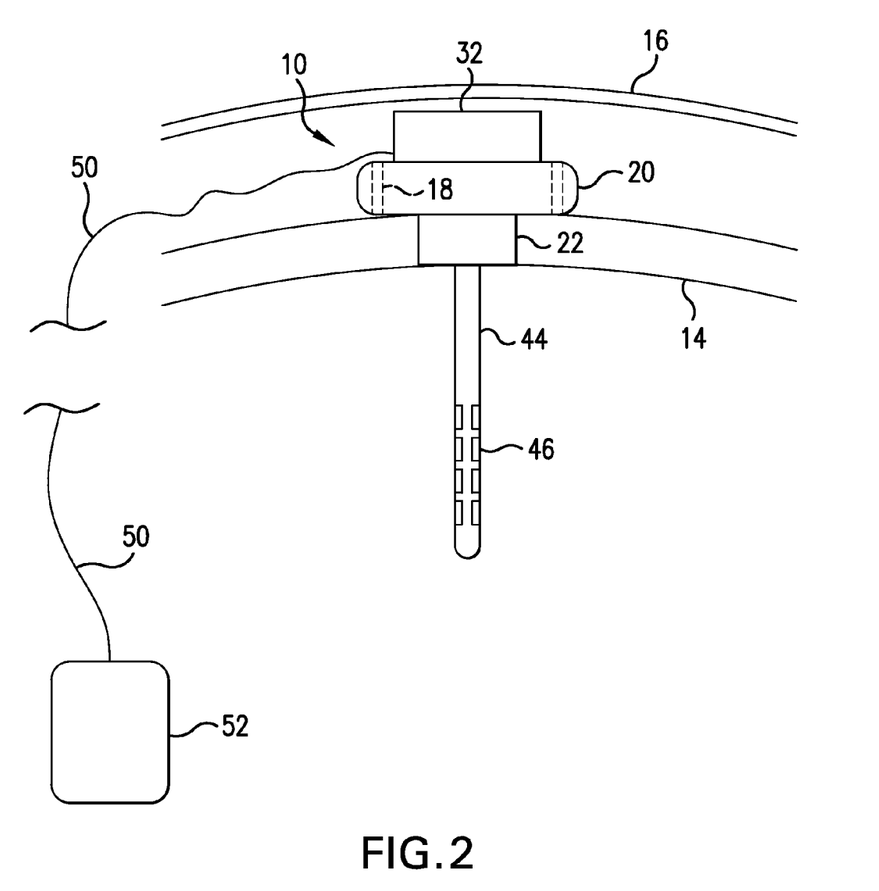
FIG. 2 shows a side view of the burr hole assembly.

FIG. 2 shows a side view of burr hole assembly 10 mounted on a patient's head with the burr hole portion implanted in the patient's skull 14 via screw holes 18 for mechanical fixation. Input/output unit 32 connects to three signal wires 42 (not shown) and lead extension 50 (not shown), which travels subcutaneously in a tunnel under the skin 16 overlying the patient's skull 14. Electrode lead 44 is inserted through and secured by the burr hole portion. Electrode lead 44 has eight directional electrodes 46 disposed thereon at a distal portion of electrode lead 44.

Figure 3:
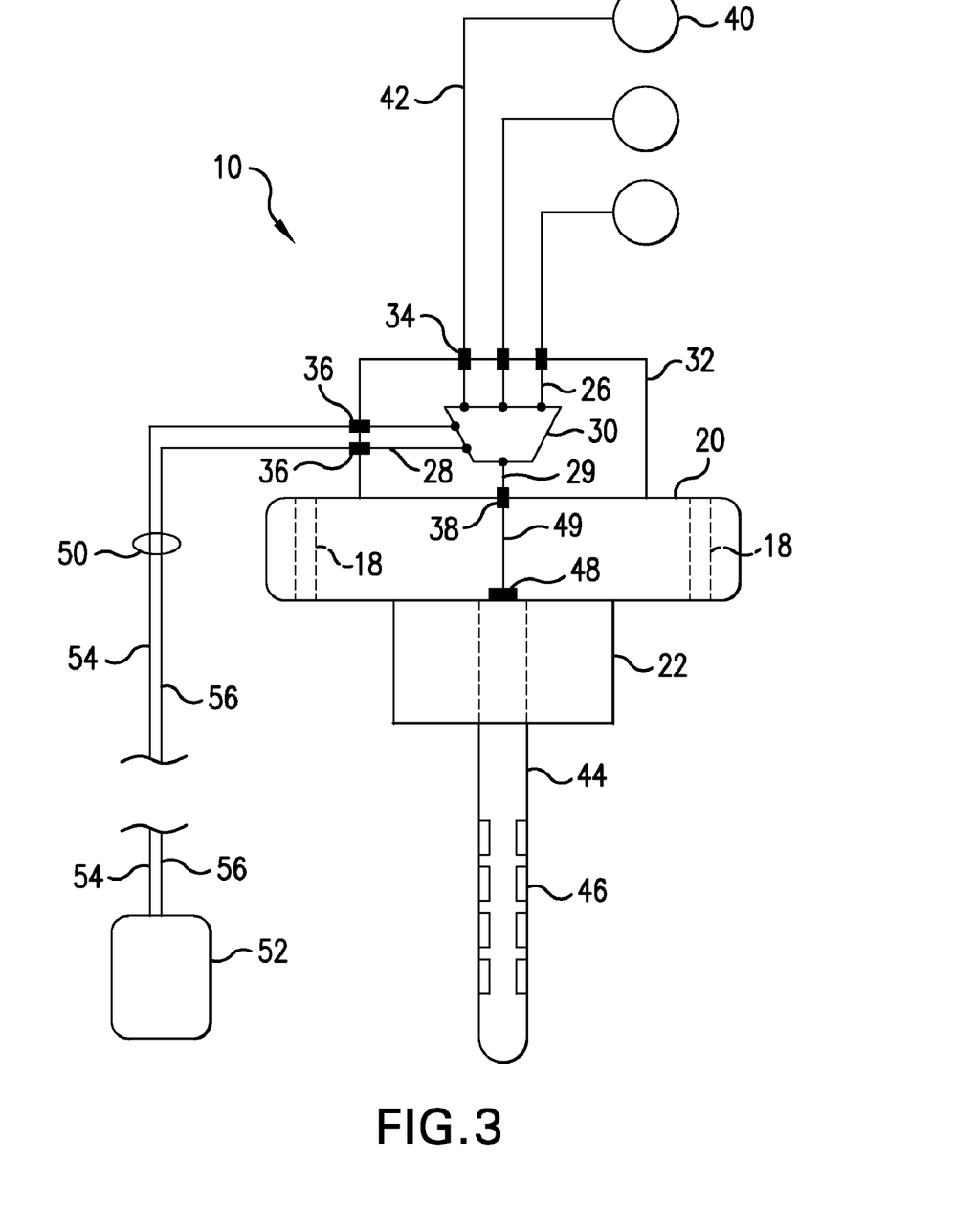
FIG. 3 shows a schematic representation of the burr hole assembly.

FIG. 3 shows a schematic representation of burr hole assembly 10. Input/output unit 32 has a sensor interface comprising three sensor ports 34 for connecting with EEG signal wires 42 and receiving input from EEG sensors 40. Input/output unit 32 also has a pulse generator interface comprising two lead extension ports 36 (or in some cases, one lead extension port) in for connecting lead extension 50 and communicating with pulse generator 52. One of the ports 36 is for connecting with a signal line 54 of lead extension 50, and the other of the ports 36 is for connecting with a pulse stimulation line 56 of lead extension 50. Signal line 54 carries signals back and forth from pulse generator 52 and input/output unit 32. Pulse stimulation line 56 carries stimulation pulses generated by pulse generator 52 to input/output unit 32. Input/output unit 32 also has an electrode lead interface comprising electrode lead port 38 for connecting with electrode lead 44 via wire 49 and electrical contact 48, which is in contact with electrode lead 44.

Contained in input/output unit 32 is a multiplexer 30, which is connected to sensor ports 34, lead extension ports 36, and electrode lead port 38 via electrical pathways 26, 28, and 29, respectively. Multiplexer 30 performs the function of selectively providing electrical connectivity between these various interfaces.

In operation, via signal line 54, pulse generator 52 transmits a signal to multiplexer 30 instructing it to route the signals from EEG sensors 40 to pulse generator 52. In response, multiplexer 30 provides the requested connection by sampling each of sensor ports 34 in a time-dependent fashion. Multiplexer 30 routes the sensor signals to the lead extension port 36 that is associated with signal line 54. Via signal line 54, the sensor signals are then transmitted to pulse generator 52, which receives and processes the sensor signal. In response to the sensor signals, pulse generator 52 adjusts the pulse stimulation (e.g., changing the pulse frequency) being generated. The pulse stimulation is carried through pulse stimulation line 56 to its associated extension lead port 36. Multiplexer 30 receives the pulse stimulation and relays it to electrode lead port 38 for transmission to electrode lead 44 via wire 49 and electrical contact 48.

Figure 4A:
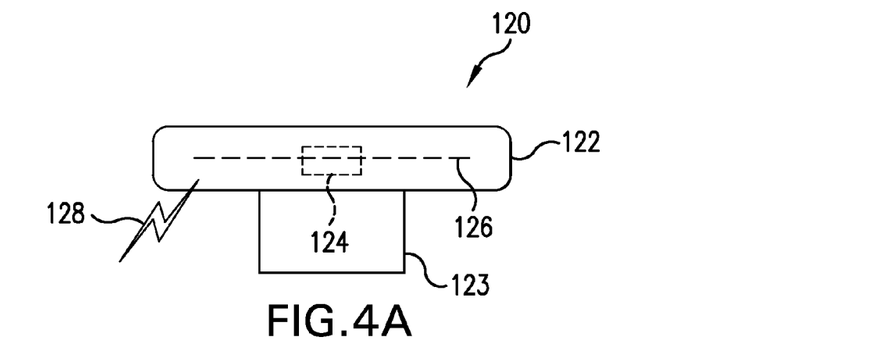
FIG. 4A shows a side view and FIG. 4B shows a top view of an example burr hole assembly according to another embodiment.
Figure 4B:
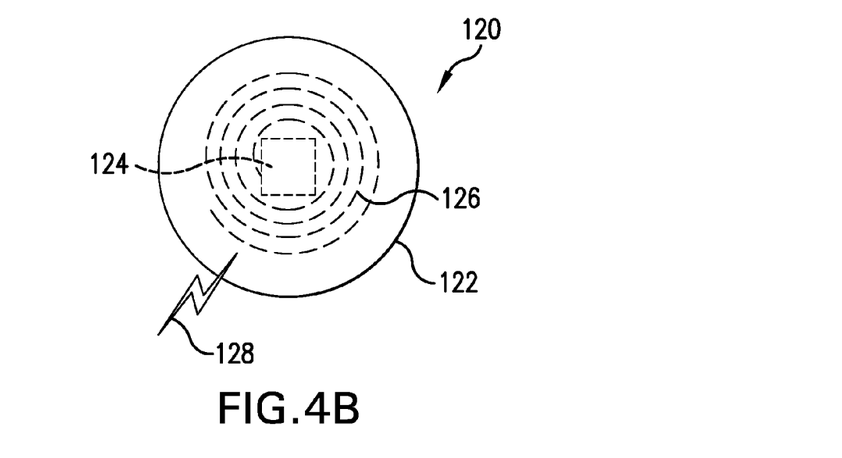

FIGS. 4A (side view) and 4B (top view) show a burr hole assembly 120 according to another embodiment of the present invention. Burr hole assembly 120 includes a burr hole portion comprising a burr hole cap 122 and a burr hole base 123. Incorporated within burr hole cap 122 is an accelerometer 124 which detects the patient's head motion. Accelerometer 124 includes an RF transceiver with a coiled wire antenna 126 for providing a wireless link 128 to communicate with components of a brain stimulation system, such as a pulse generator or an external control system for the pulse generator. By multiplexing, coiled wire antenna 126 can also serve as a recharging coil for external recharging of the pulse generator.

Figure 5:
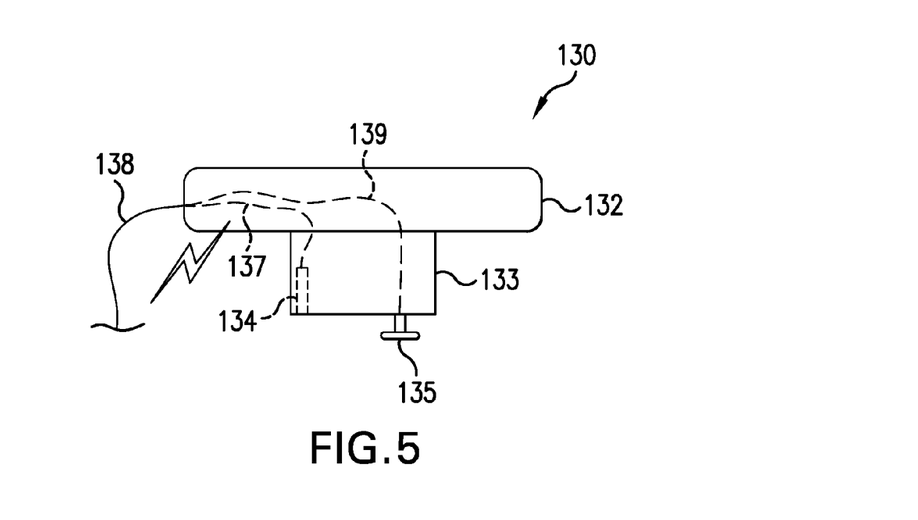
FIG. 5 shows a side view of an example burr hole assembly according to yet another embodiment.

FIG. 5 shows a side view of a burr hole assembly 130 according to yet another embodiment of the present invention. Burr hole assembly 130 includes a burr hole portion comprising a burr hole cap 132 and a burr hole base 133. Incorporated within burr hole base 133 is an intracranial pressure sensor 134 which measures intracranial fluid pressures and an EEG sensor 135. Pressure sensor 134 and EEG sensor 135 transmit signals to a pulse generator via a transmission line 137 and 139, respectively. Transmission lines 137 and 139 travel in a wire 138, which may or may not be contained in a lead extension.

MRI scanners are widely used in brain imaging. However, the electromagnetic fields generated by an MRI scanner can create a problem for implanted medical devices. For brain stimulation systems, the electromagnetic field may induce electric currents in the electrodes, causing unwanted heating of the electrodes. Therefore, in certain embodiments, the burr hole assembly may further include a system for attenuating unwanted electric currents in the brain stimulation system when the patient is undergoing MRI scanning. This feature may be useful in making the brain stimulation system more compatible with MRI scanners.

Various types of systems for attenuating the effects of MRI-generated electromagnetic fields are known in the art, including those described in U.S. Pat. No. 7,050,855 (Zeiklemaker et al.) and U.S. Pat. No. 7,174,219 (Wahlstrand et al.). Such systems can employ circuits that block MRI-specific frequency ranges using various conventional electronic components such as band-pass filters, capacitors, or current chokes; and may further incorporate magnetic field detectors that measure the strength of the MRI-generated electromagnetic field.

This first aspect of the present invention may also be combined with any of the features of the second aspect of the present invention, as described below.

In a second aspect of the present invention, the burr hole assembly is designed to operate in cooperation with an electrode lead having a directional electrode. As such, the burr hole assembly includes a rotation mechanism to allow the user to rotate the electrode lead about its central longitudinal axis so that the directional electrode is oriented in the desired direction.

The rotation mechanism is engageable with the electrode lead and rotates the electrode lead under manual, automatic, or semi-automatic control. In some cases, the rotation mechanism uses an electromechanical drive system which can include any of various electromechanical components such as microdrives, manual micropositioners, hydraulic micropositioners, threaded-screw positioners, stepper motors, electrically-powered gears, linear actuators, or solenoids. In some cases, the rotation mechanism may further contain mechanisms for adjusting the x, y, z positions and angulation of the electrode lead, such as the mechanism described in U.S. Pat. No. 6,491,699 (Henderson et al.).

In certain embodiments, the burr hole assembly includes a control system which is coupled to and in communication with the rotation mechanism. The control system may control various parameters in the operation of the rotation mechanism, including the rotation speed, power, torque, and/or acceleration. Where the rotation mechanism uses an electric motor, various types of motor control systems known in the art are suitable for use in the control system. Such motor control systems may have circuitry that operates the rotation mechanism by providing control signals (digital or analog) to the rotation mechanism, or by varying the drive mode (e.g., continuously or step-wise), input power, input frequency, or driving current waveform that is provided to the motor in the rotation mechanism.

In certain embodiments, the rotation mechanism may also include a position transducer which detects the rotational position of the electrode lead. The position transducer can employ any of various types of position sensing components that are known in the art, including mechanical, electrical (e.g., using a variable resistor or induction coil), electromechanical (e.g., using switches), or optical components (e.g., using laser tracking). According to the detected rotational position of the electrode lead, the position transducer generates a signal, which may be analog or digital. The position transducer, which is coupled to and in communication with the control system, transmits the signal to the control system. The control system, which can include an analog-to-digital converter, receives the position signal from the position transducer. The control system processes the position signal and controls the operation of the rotation mechanism according to a pre-determined program. In some cases, the control system may include a microprocessor system (e.g., a desktop PC) for further controlling the rotation mechanism, for receiving user input, and/or for providing a graphical display of the rotational position of the electrode lead.

Figure 6:
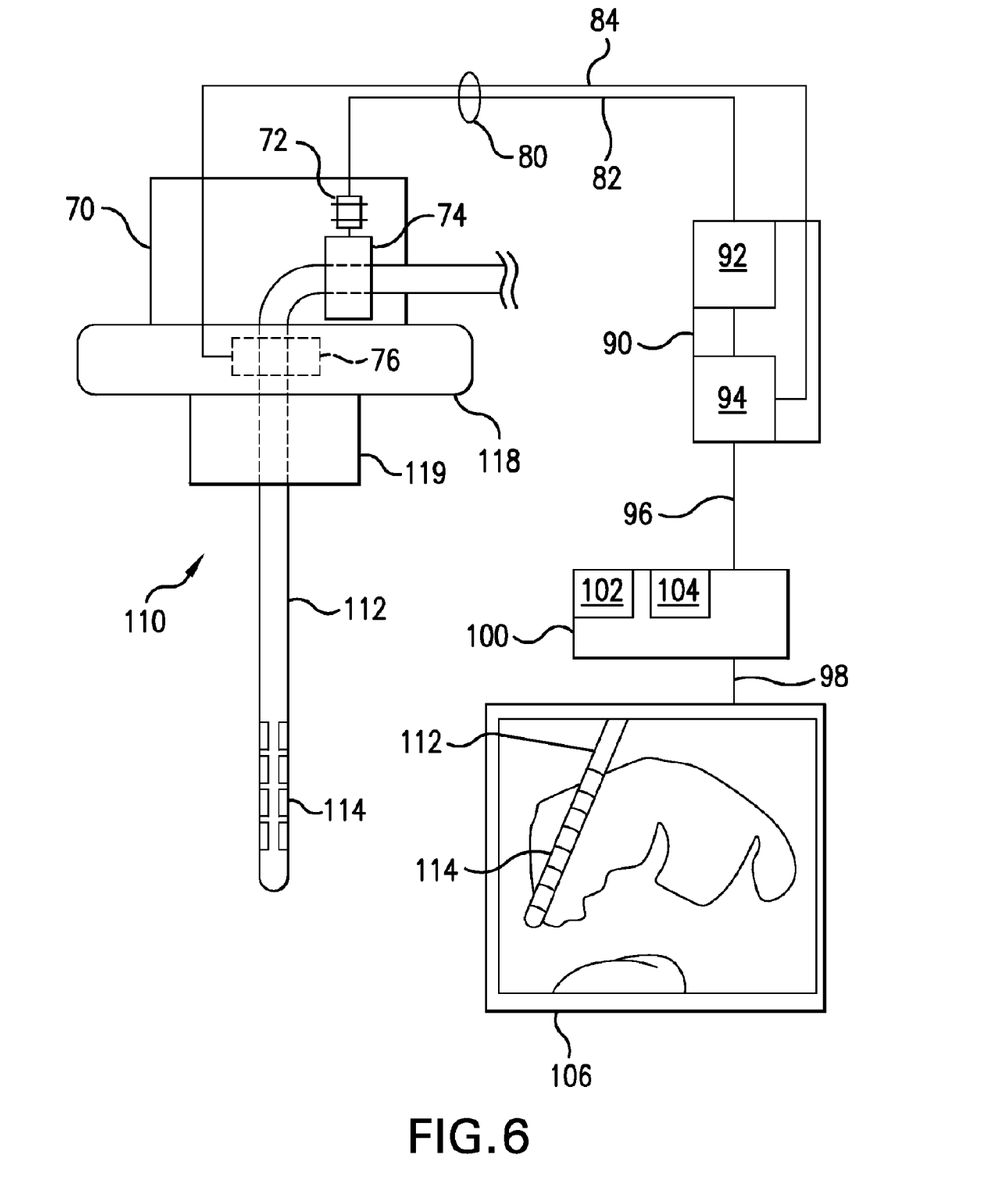
FIG. 6 shows a schematic representation of an example burr hole assembly according to yet another embodiment.

FIG. 6 shows a schematic representation of a burr hole assembly 110 according to another embodiment of present invention. Burr hole assembly 110 includes a burr hole portion comprising a burr hole cap 118 and a burr hole base 119. An L-shaped electrode lead 112 having eight directional electrodes 114 is inserted through and secured by the burr hole portion. Mounted on burr hole cap 118 is a rotation mechanism 70 comprising a gear mechanism 74 and a DC servo motor 72 for driving gear mechanism 74. Gear mechanism 74 is mechanically engaged with electrode lead 112 so that rotation of electrode lead 112 is driven by servo motor 72. Gear mechanism 74 may use any of various types of gear systems for providing rotational motion, including spur gears, bevel gears, rack-and-pinion gears, worm gears, etc. Distal to the bend, electrode lead 112 travels through a guide channel 76 that guides the distal portion of electrode lead 112 through burr hole cap 118 while allowing rotation of electrode lead 112 to prevent twisting or breaking of electrode lead 112. Guide channel 76 may simply be a pass-through channel for electrode lead 112 or may contain gears that engage electrode lead 112. Guide channel 76 also includes a position sensing transducer which senses the rotational position of electrode lead 112. In some cases, guide channel 76 may have a gear system that is driven by a motor to provide coordinated rotation with gear mechanism 74 to prevent twisting or breaking of electrode lead 112 as it is being rotated.

A cable 80, containing a power line 82 and a signal line 84, connects rotation mechanism 70 to a motor control unit 90. Via power line 82, servo motor 72 is connected to a power converter 92 contained in motor control unit 90. Via signal line 84, the position sensing transducer in guide mechanism 76 is connected to a motor control circuit 94 contained in motor control unit 90. Under the command of motor control circuit 94, power converter 92 provides power output to servo motor 72 via power line 82. Motor control circuit 94 also receives position signal data from the position sensing transducer via signal line 84, and in response, adjusts the power output of power converter 92.

Via a cable 96 (e.g., a USB cable), motor control unit 90 is connected to and in communication with a conventional computer system 100 containing a microprocessor 102 and memory 104. Memory 104 is loaded with software which is configured to establish an orthogonal three-dimensional coordinate system and receive position information from the position sensing transducer via motor control circuit 94. A mapping function is then used to translate the rotational position into the reference frame of the stored coordinate system containing the fixed anatomic structures and/or other fiducial references (e.g., the AC-PC plane of the brain, or the neurosurgical stereotactic headframe). A three-dimensional composite image is then displayed on a display screen 106 connected via cable 98. This three-dimensional image can be manipulated to provide various views, including coronal, sagittal, and axial views. Computer system 100 also includes an input device (e.g., keyboard or mouse, not shown) for receiving instructions from the user (e.g., the desired rotation angle).

In operation, the electrode lead is inserted into the brain and the burr hole assembly is mounted on the patient's head to secure the electrode lead. The position sensing transducer reads the rotational position of electrode lead 112, and this information is transmitted via motor control unit 90 to microprocessor system 100. Computer system 100 processes the position data and displays a 3-D representation of electrode lead 112 and directional electrodes 114 on display screen 106. Based on this visual representation, the user inputs the rotation angle (via a keyboard, mouse, etc.) into computer system 100.

The user's input is processed by computer system 100, which then instructs motor control unit 90 to rotate electrode lead 112 in the desired direction. Motor control circuit 94 receives the instructions and activates power converter 92 to provide the appropriate amount of power to servo motor 72 for the appropriate duration of time to rotate electrode lead 112. Additional fine adjustments are made using a feedback loop in which the position sensing transducer continues to return position information to motor control circuit 94, which then makes further rotation adjustments as needed, until the desired rotation angle for electrode lead 112 is achieved.

In certain embodiments, the burr hole assembly may further include a system for attenuating currents in the electrode lead that are induced by an MRI scanner, as described above.

This second aspect of the present invention may also be combined with any of the features of the first aspect of the present invention, as described above.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention.

We claim:

1. A burr hole assembly that operates in cooperation with a brain stimulation system, wherein the burr hole assembly comprises:
   a burr hole portion adapted to secure an electrode lead that is inserted into the brain;
   one or more sensors mounted directly on the burr hole portion, wherein the one or more sensors are for monitoring a patient's clinical status and are capable of being coupled to the brain stimulation system, and
   an input/output unit mounted on the burr hole assembly for providing a coupling between the one or more sensors and the brain stimulation system, said input/output unit comprising an electrode lead interface for coupling with an electrode lead in the brain stimulation system, a pulse generator interface for coupling with a pulse generator in the brain stimulation system, and a multiplexer for providing electrical connectivity between the electrode lead interface and the pulse generator interface.

2. The burr hole assembly of claim 1, wherein the input/output unit further includes a sensor interface for coupling with the one or more sensors.

3. The burr hole assembly of claim 2, wherein the multiplexer further provides electrical connectivity between the sensor interface and the pulse generator interface.

4. The burr hole assembly of claim 3, wherein the multiplexer receives signals from the pulse generator via the pulse generator interface, and in response to the signals, selectively provides electrical connectivity between the pulse generator interface and the sensor interface.

5. The burr hole assembly of claim 1, wherein the pulse generator interface includes a port for connecting with a lead extension in the brain stimulation system.

6. The burr hole assembly of claim 1, wherein the pulse generator interface includes one or more communication ports for communicating with the pulse generator, and a stimulation port for receiving stimulation pulses from the pulse generator.

7. The burr hole assembly of claim 1, wherein the one or more sensors is selected from the group consisting of: motion sensors, temperature sensors, intracranial pressure sensors, force sensors, and cardiovascular sensors.

8. The burr hole assembly of claim 1, further comprising an additional sensor coupled to the brain stimulation system via a wireless link.

9. The burr hole assembly of claim 1, wherein the burr hole assembly further comprises a system for attenuating electrical currents induced by an electromagnetic field that are generated by an MRI scanner.

10. The burr hole assembly of claim 1, wherein the burr hole portion comprises a burr hole cap adapted to fit over a burr hole.

11. The burr hole assembly of claim 10, wherein the one or more sensors are mounted directly on the burr hole cap.

12. The burr hole assembly of claim 1, wherein the burr hole portion comprises a burr hole base adapted to fit within a burr hole.

13. The burr hole assembly of claim 12, wherein the one or more sensors are mounted directly on the burr hole base.

14. The burr hole assembly of claim 1, wherein the one or more sensors are electroencephalogram (EEG) sensors.

15. A burr hole assembly for operating in cooperation with an electrode lead having one or more directional electrodes, wherein the burr hole assembly comprises:
the burr hole portion of claim 1; and
a rotation mechanism adapted to rotate the electrode lead.

16. The burr hole assembly of claim 15, wherein the rotation mechanism has an electromechanical drive system.

17. The burr hole assembly of claim 16, wherein the electromechanical system includes a servo motor.

18. The burr hole assembly of claim 15, further comprising a control system for controlling the rotation mechanism, wherein the control system is coupled to the rotation mechanism.

19. The burr hole assembly of claim 18, further comprising a position transducer for detecting the rotational position of the electrode lead, wherein the position transducer is coupled to the control system.

20. The burr hole assembly of claim 19, wherein the control system includes a computer system for providing a user interface.

21. The burr hole assembly of claim 20, wherein the computer system is coupled to the position transducer and includes a graphical display for displaying the rotational position of the electrode lead.

22. The burr hole assembly of claim 15, wherein the rotation mechanism is mounted on the burr hole portion.

23. The burr hole assembly of claim 15, wherein the burr hole assembly further comprises a system for attenuating electrical currents induced by an electromagnetic field that are generated by an MRI scanner.

24. A system comprising:
an electrode lead;
the burr hole portion of the burr hole assembly of claim 1 for receiving the electrode lead; and
a pulse generator for providing stimulation pulses to the electrode lead.

25. The system of claim 24, wherein the electrode lead has one or more directional electrodes.

26. The system of claim 24, further comprising an external control system that is coupled to the pulse generator, wherein the external control system controls the operation of the pulse generator.

27. The system of claim 26, wherein the coupling is a wireless link.

28. The system of claim 24, further comprising a lead extension for providing electrical connectivity between the pulse generator and the input/output unit.

29. The system of claim 24, further comprising a system for attenuating electrical currents induced by an electromagnetic field that are generated by an MRI scanner.

30. The system of claim 24, further comprising a rotation mechanism mounted on the burr hole portion and connected to the electrode lead.

31. A system comprising:
an electrode lead having one or more directional electrodes;
the burr hole portion of the burr hole assembly of claim 1 to receive the electrode lead; and
a rotation mechanism associated with the burr hole portion and connected to the electrode lead.

32. The system of claim 31, further comprising a pulse generator electrically connected to the electrode lead.

33. The system of claim 32, further comprising a lead extension for providing electrical connectivity between the electrode lead and the pulse generator.

34. The system of claim 31, further comprising a control system for controlling the rotation mechanism, wherein the control system is coupled to the rotation mechanism.

35. The system of claim 34, further comprising a position transducer for detecting the rotational position of the electrode lead, wherein the position transducer is coupled to the control system.

36. The system of claim 35, wherein the control system includes a computer system for providing a user interface.

37. The system of claim 36, wherein the computer system is coupled to the position transducer and includes a graphical display for displaying the rotational position of the electrode lead.

38. The system of claim 31, further comprising a system for attenuating electrical currents induced by an electromagnetic field that are generated by an MRI scanner.

* * * * *